(12) United States Patent
Haddad et al.

(10) Patent No.: US 7,036,362 B2
(45) Date of Patent: May 2, 2006

(54) DOWNHOLE DETERMINATION OF FORMATION FLUID PROPERTIES

(75) Inventors: Sammy S. Haddad, Mandeville, LA (US); Erik Rylander, Harvey, LA (US); Rahul Joshi, Tulsa, OK (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/248,437

(22) Filed: Jan. 20, 2003

(65) Prior Publication Data

US 2004/0139798 A1      Jul. 22, 2004

(51) Int. Cl.
*E21B 49/00*      (2006.01)

(52) U.S. Cl. .................................................. 73/152.05

(58) Field of Classification Search .............. 73/152.42, 73/152.18, 152.22, 152.02, 152.05, 152.51
See application file for complete search history.

(56) References Cited

U.S. PATENT DOCUMENTS

| | | | | |
|---|---|---|---|---|
| 3,003,554 | A | * | 10/1961 | Craig, Jr. et al. ............ 166/402 |
| 3,011,554 | A | * | 12/1961 | Desbrandes et al. ......... 166/100 |
| 3,604,256 | A | | 9/1971 | Prats |
| 3,839,914 | A | * | 10/1974 | Modisette et al. ............ 73/438 |
| 3,934,468 | A | | 1/1976 | Brieger |
| 4,287,946 | A | * | 9/1981 | Brieger ....................... 166/100 |
| 4,384,472 | A | * | 5/1983 | Tournier ..................... 73/30.01 |
| 4,495,805 | A | | 1/1985 | Dowling et al. |
| 4,535,851 | A | | 8/1985 | Kirkpatrick et al. |
| 4,750,351 | A | * | 6/1988 | Ball ............................ 73/54.04 |
| 4,821,564 | A | | 4/1989 | Pearson et al. |
| 4,843,878 | A | | 7/1989 | Purfurst et al. |
| 4,860,581 | A | | 8/1989 | Zimmerman et al. |
| 5,042,296 | A | | 8/1991 | Burgess |
| 5,079,750 | A | * | 1/1992 | Scherbatskoy ................ 367/85 |
| 5,622,223 | A | | 4/1997 | Vasquez |
| 6,092,416 | A | * | 7/2000 | Halford et al. ........... 73/152.23 |
| 6,157,893 | A | | 12/2000 | Berger et al. |
| 6,178,815 | B1 | | 1/2001 | Felling et al. |
| 6,250,138 | B1 | | 6/2001 | Shwe et al. |
| 6,272,934 | B1 | * | 8/2001 | Rajan et al. .............. 73/861.04 |

(Continued)

FOREIGN PATENT DOCUMENTS

| | | | |
|---|---|---|---|
| GB | 2 177 803 A | | 1/1987 |
| GB | 2177803 A | * | 1/1987 |

(Continued)

*Primary Examiner*—Hezron Williams
*Assistant Examiner*—John Fitzgerald
(74) *Attorney, Agent, or Firm*—J. L. Jennie Salazar; Victor H. Segura; Brigitte L. Echols

(57) ABSTRACT

A method is disclosed for determining viscosity and density of fluid from formations surrounding an earth borehole, including the following steps: (a) suspending a formation testing device in the borehole; (b) drawing formation fluid into the device; (c) causing the fluid to flow in a flow line under a first set of conditions; (d) causing the fluid to flow in the flow line under a second set of conditions; (e) measuring a first fluid pressure differential in the flow line during fluid flow under the first set of conditions, and measuring a second pressure differential in the flow line during fluid flow under the second set of conditions; and (f) determining density and viscosity of the fluid as a function of the first and second measured pressure differentials.

29 Claims, 7 Drawing Sheets

U.S. PATENT DOCUMENTS

| | | | |
|---|---|---|---|
| 6,450,259 B1 * | 9/2002 | Song et al. | 166/255.1 |
| 6,474,152 B1 * | 11/2002 | Mullins et al. | 73/152.22 |
| 6,755,079 B1 * | 6/2004 | Proett et al. | 73/152.18 |
| 6,938,470 B1 * | 9/2005 | DiFoggio et al. | 73/152.24 |

FOREIGN PATENT DOCUMENTS

| | | |
|---|---|---|
| WO | WO 01/51898 | 7/2001 |
| WO | WO 01/73400 A1 | 10/2001 |

* cited by examiner

DOWNHOLE DETERMINATION OF FORMATION FLUID PROPERTIES

BACKGROUND OF INVENTION

1. Field of the Invention

This invention relates to the field of testing formations surrounding an earth borehole with a formation testing tool to obtain fluid samples and, more particularly, to improvements in downhole determination of formation fluid properties.

2. Background of the Invention

Existing well logging devices can provide useful information about hydraulic properties of formations, such as pressures and fluid flow rates, and can obtain formation fluid samples, generally for uphole analysis. Reference can be made, for example, to U.S. Pat. Nos. 3,934,468 and 4,860,581. In a logging device of this general type, a setting arm or setting pistons can be used to controllably urge the body of the logging device against a side of the borehole at a selected depth. The side of the device that is urged against the borehole wall typically includes a packer which surrounds a probe. As the setting arm extends, the probe is inserted into the formation, and the packer then sets the probe in position and forms a seal around the probe, whereupon formation pressure can be measured and fluids can be withdrawn from the formation.

Wireline formation testing, in general, strives to provide, inter alia, a measurement of the formation mobility. Formation mobility is defined as the formation permeability, measured in darcy, divided by fluid viscosity, measured in centipoise. The value of fluid viscosity, under in situ conditions of pressure and temperature, is usually unknown. However, to be able to accurately identify the local formation permeability, knowledge of viscosity is required. Knowledge of fluid density measurement would also be very helpful, for example in identifying fluid type or types.

Downhole determination (i.e., performed, in whole or in part, while the tool is downhole) of properties of sampled fluids, including density and viscosity, has been proposed in the prior art. This would permit greater flexibility in measuring and/or determining fluid properties, at essentially in situ conditions and, on fluid samples from various depth levels. However, equipment and techniques contemplated for achieving same, suffer one or more of the following disadvantages: undue complexity, inaccuracy or unreliability of measurement, and/or incompatibility or difficulty of adaptation for use with existing formation testing tools.

It is among the objects of the present invention to provide an improved method and apparatus for downhole determination of properties of sampled borehole fluids.

SUMMARY OF INVENTION

Viscosity and density could theoretically be determined by obtaining the pressure readings across any two points in the flow line and using a pressure drop equation to calculate the fluid properties. However, there is only one equation and there are two unknowns.

In accordance with a form of the invention, a method is provided for determining viscosity and density of fluid from formations surrounding an earth borehole, comprising the following steps: (a) suspending a formation testing device in the borehole; (b) drawing formation fluid into the device; (c) causing the fluid to flow in a flow line under a first set of conditions; (d) causing the fluid to flow in the flow line under a second set of conditions; (e) measuring a first fluid pressure differential in the flow line during fluid flow under the first set of conditions, and measuring a second pressure differential in the flow line during fluid flow under the second set of conditions; and (f) determining density and viscosity of the fluid as a function of the first and second measured pressure differentials.

An embodiment of this form of the invention includes the following steps: (a) suspending a formation testing device in the borehole (b) drawing formation fluid into the device; (c) causing the fluid to flow in a flow line in the device at a first flow rate and through a first constriction, and measuring a first pressure differential on opposing sides of the constriction; (d) causing the fluid to flow in a flow line of device at a second flow rate and through a second constriction, and measuring a second pressure differential on opposing sides of the second constriction; and (e) determining the density and viscosity of the fluid as a function of the first and second measured pressure differentials. In this embodiment, the step of determining density and viscosity includes deriving a first expression for the first measured pressure differential as a function of unknown fluid viscosity and fluid density at the first flow rate and deriving a second expression for the second measured pressure differential as a function of unknown fluid viscosity and fluid density at the second flow rate, and solving the first and second expressions to determine fluid viscosity and fluid density. The steps (b) through (e) can be repeated at different depth levels in the borehole to determine the density and viscosity of fluid at such different depth levels in the formations.

Further features and advantages of the invention will become more readily apparent from the following detailed description when taken in conjunction with the accompanying drawings.

DETAILED DESCRIPTION

Figure 1:
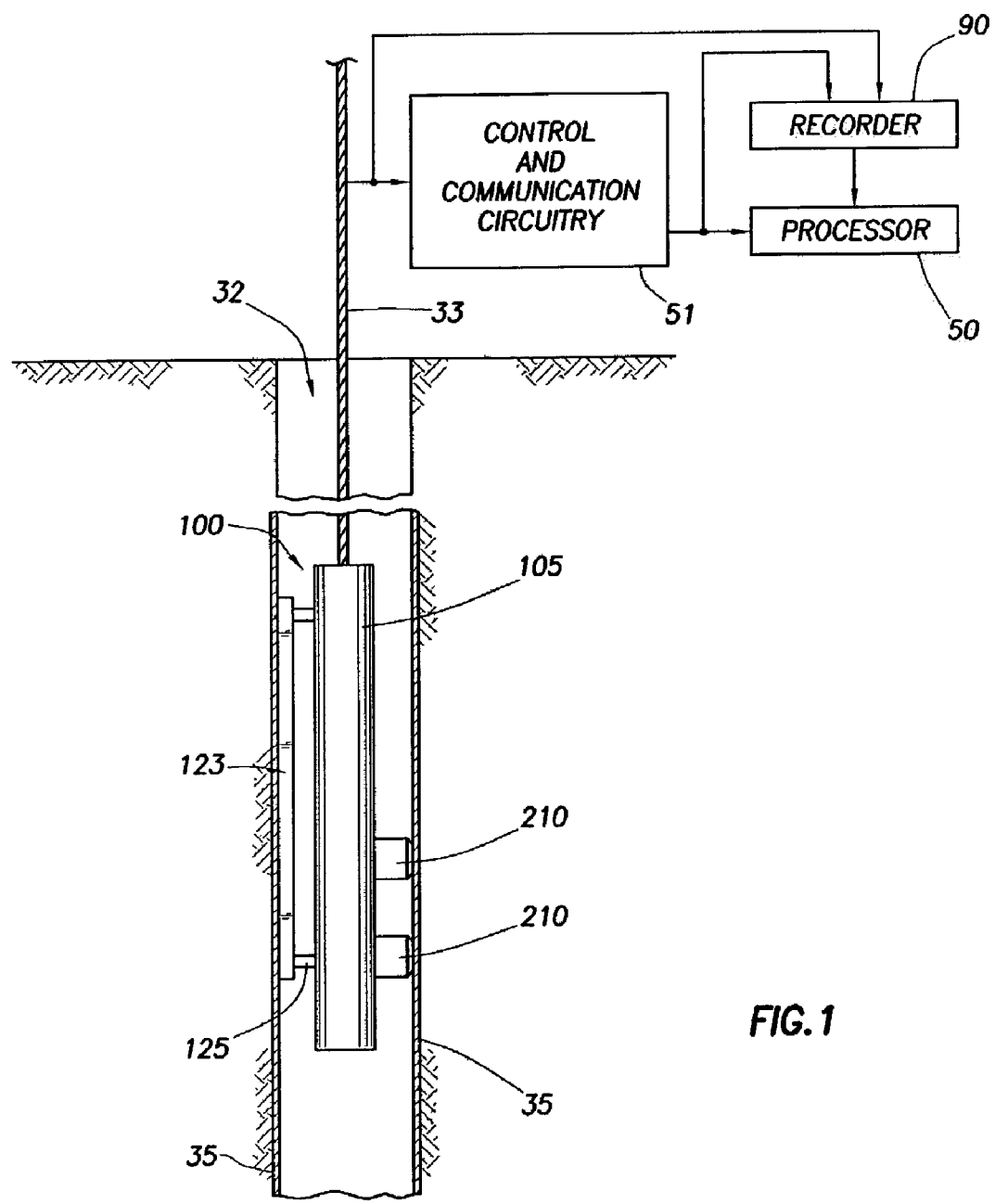
FIG. 1 is a diagram, partially in block form, of a logging device in which embodiments of the invention can be employed.

Referring to FIG. 1 there is shown a representative embodiment of a formation tester apparatus for investigating subsurface formations 31 traversed by a borehole 32, which can be used in practicing embodiments of the invention. The borehole 32 is typically filled with drilling fluid or mud which contains finely divided solids in suspension. A mudcake on the borehole wall is represented at 35. The investigating apparatus or logging device 100 is suspended in the borehole 32 on an armored multiconductor cable 33, the length of which substantially determines the depth of the device 100. Known depth gauge apparatus (not shown) is provided to measure cable displacement over a sheave wheel (not shown) and thus the depth of logging device 100 in the borehole 32. The cable length is controlled by suitable means at the surface such as a drum and winch mechanism (not shown). Circuitry 51, shown at the surface although portions thereof may typically be downhole, represents control and communication circuitry for the logging apparatus. Also shown at the surface are processor 50 and recorder 90. These may all generally be of known type.

The logging device or tool 100 has an elongated body 105 which encloses the downhole portion of the device, controls, chambers, measurement means, etc. One or more arms 123 can be mounted on pistons 125 which extend, e.g. under control from the surface, to set the tool. The logging device includes one or more probe modules each of which includes a probe assembly 210 which is movable with a probe actuator (not separately shown) and includes a probe (not separately shown) that is outwardly displaced into contact with the borehole wall, piercing the mudcake and communicating with the formations. The equipment and methods for taking pressure measurements and doing sampling are well known in the art, and the logging device 100 is provided with these known capabilities. Reference can be made, for example, to U.S. Pat. Nos. 3,934,468 and 4,860,581, which describe early versions of devices of this general type.

Modern commercially available services utilizing, for example, a modular formation dynamics tester ("MDT"—trademark of Schlumberger), can provide a variety of measurements and samples, as the tool is modularized and can be configured in a number of ways. Examples of some of the modules employed in this type of tool, are as follows: An electric power module is generally provided. It does not have a flowline or hydraulic bus, and will typically be the first (top) module in the string. A hydraulic power module provides hydraulic power to all modules that may require same, and such power can be propagated via a hydraulic bus. Probe modules, which can be single or plural probes, includes pistons for causing engagement of probe(s) for fluid communication with the formations. Sample modules contain sample chambers for collecting samples of formation fluids, and can be directly connected with sampling points or connected via a flowline. A pumpout module can be used for purging unwanted fluids. An analyzer module uses optical analysis to identify certain characteristics of fluids. A packer module includes inflatable packer elements which can seal the borehole circumference over the length of the packer elements. Using the foregoing and other types of modules, the tool can be configured to perform various types of functions.

The present invention has application to tool configurations which draw formation fluid into the tool.

Figure 2:
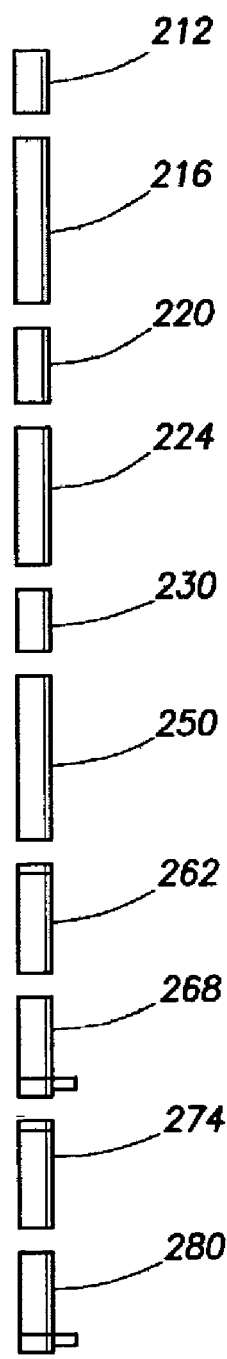
FIG. 2 is a block diagram of an example of a modular tool in which embodiments of the invention can be employed.

Referring to FIG. 2, there is shown an example of a formation tester tool string in which embodiments of the invention can be employed. It is emphasized, that this particular configuration is an example, and the invention has application to many other tool configurations, modular or otherwise. In FIG. 2, 212 represents an electronics module that provides electrical power and control. The module 216 is of the type that contains an exit port (for returning formation fluids to the borehole) and a plurality of bottles for collecting samples. The module 220 is of the type that contains a single large volume bottle or receptacle for sampling. The module 224 is a pumpmodule, and the module 230 is a fluid analyzer module, for example of the optical type noted briefly above. The module 250 is the type of module that typically contains several (e.g. six) sample chambers or bottles, each capable of holding a sample of, for example, 450 cc. The blocks 262 and 274 are hydraulic power and control modules, and the modules 268 and 280 are pad/probe modules.

As an example of a type of job that includes sampling, the tool is set, a pretest is taken, the pump is turned on and the formation fluid goes through the flow line of all the modules until reaching the exit port at which, after the contamination level reaches an acceptable level (as monitored by the fluid analyzer module), the exit port is shut off and the sample is routed into a chamber (for example, one of the bottles in module 250 and/or the large volume sample chamber of module 220).

Figure 3:
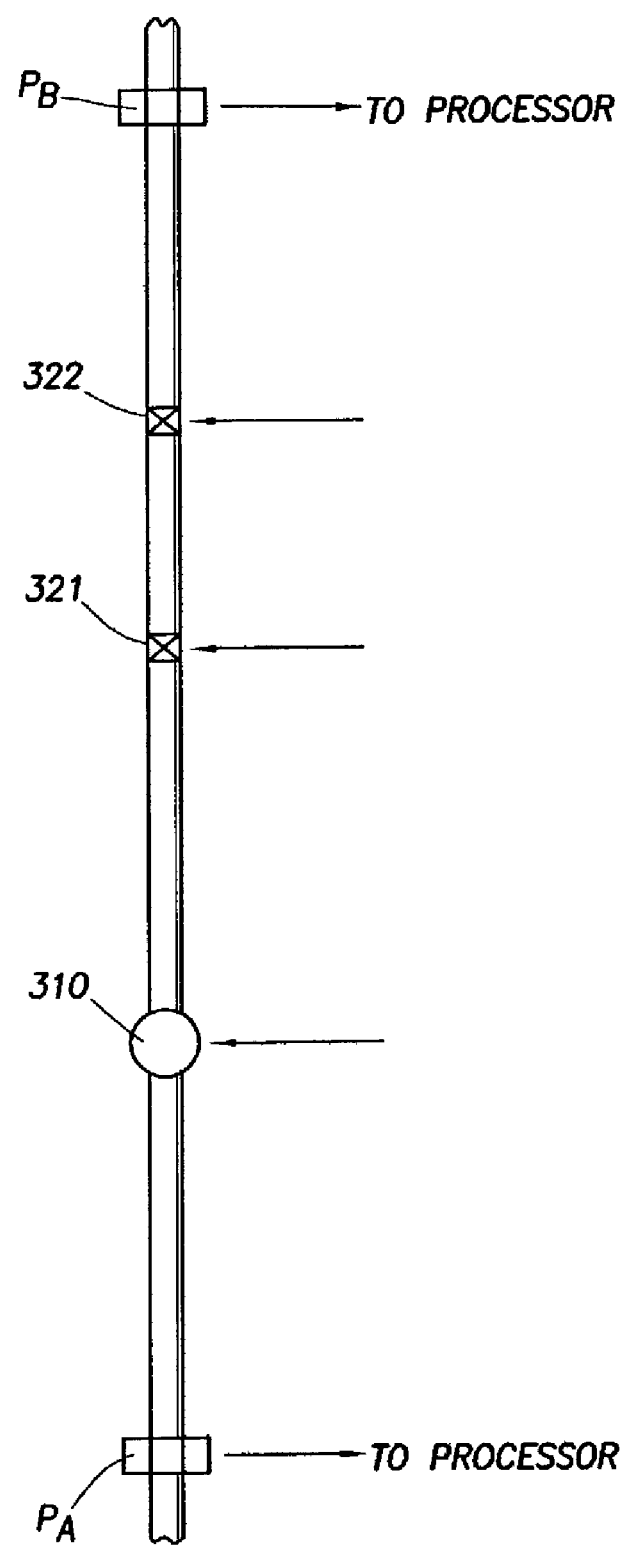
FIG. 3 is a block diagram of a portion of a system employing an embodiment of the invention.
Figure 4:
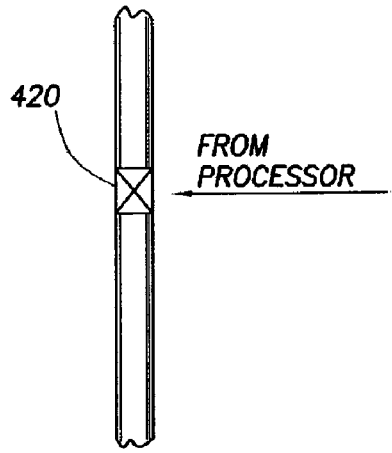
FIG. 4 is a diagram showing a portion of an alternative embodiment of the invention.
Figure 5:
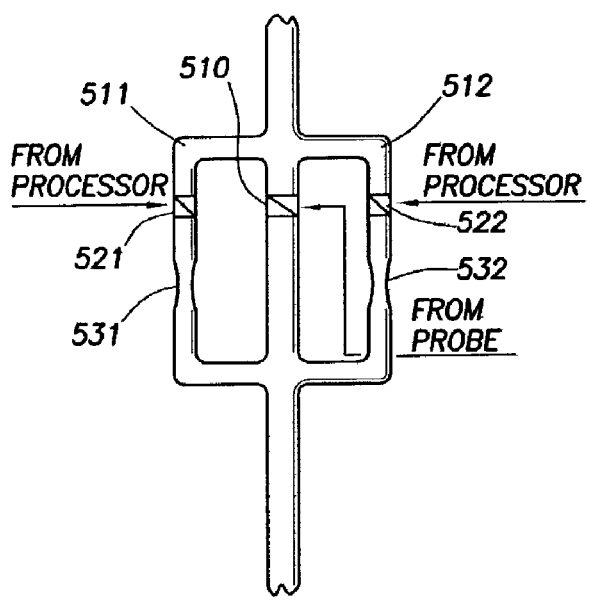
FIG. 5 is a diagram showing a portion of another alternative embodiment of the invention.

FIG. 3 shows a portion of a flow line in the apparatus of FIGS. 1 and 2, which has been adapted in accordance with an embodiment of the invention. A pump 310 under control of the processor (downhole and/or uphole), can operate to produce a desired flow rate in the flow line. Chokes 321 and 322, each also under processor control are in series in the flow line. When in their respective closed positions, the chokes have selected, and different, open cross-sectional areas for flow, so that each choke can provide a different predetermined constriction in the flow line. Pressure gauges $P_A$ and $P_B$ are provided on opposing sides of the chokes. It will be understood that other techniques can be utilized to obtain different selected constrictions for the different operating conditions employed in the present invention. For example, in FIG. 4, a single choke 420 in the flow line has three positions: open; closed with a first constriction cross-sectional flow area; and closed with a second constriction cross-sectional flow area. As another example, in FIG. 5, the flow line has a switched valve 510, and arms 511 and 512 have respective switched valves 521 and 522. The flow arms 511 and 512 are identical except that each has a different size restriction, 531 and 532, respectively. For normal flow, only valve 510 is opened. For one first constriction condition, only valve 521 in opened, and for a second constriction condition, only valve 522 is opened.

The relationship between pressure drop and viscosity and density of a fluid flowing through an orifice will next be treated. The calculations are based on given values of flow rate, pressure drop, pipe length and certain other values. The pressure drop in pipe is due to the following factors.

1. Pressure drop due to viscous resistance for flow in pipe.
2. Pressure drop across the orifice.
3. Pressure drop due to gravity (elevation) Hence the equation for total pressure drop can be written as:

$$\Delta P = \Delta Pf + \Delta Pel + \Delta Por \tag{1}$$

The gravitational pressure drop (elevation) is given by $$\Delta Pel = \rho g h \sin\theta \tag{2}$$

The fluid is assumed to be Newtonian and the pressure drop equation for friction pressure drop (only laminar) is given as:

$$\Delta Pf = \frac{32\,\mu V}{D^2} \qquad L(3a)$$

L (3a)

If, however, the flow is turbulent (Reynolds Number>2100), then the friction factor needs to be calculated. For Reynolds number less than 100,000, the friction factor can be approximated as $$f = 0.0791 Re^{-0.25}$$

(3b) where Re is Reynolds number.

The pressure drop can then be calculated as $$\Delta Pf = \frac{2f\rho V^2}{D} L \quad (3c)$$

(3c)

The pressure drop equation across the orifice is given a $$\Delta Por = \frac{Q^2(1-\beta^4)\rho}{2(CA)^2} \quad (4)$$

Using the above three equations the total pressure drop can be calculated. In the configuration of FIG. 3, a pump 310 provides differential pressure based on pumpout duty cycle and flow rate. Also, the two chokes (321, 322) of different diameters are used in formulating two independent pressure drop equations from which both density and viscosity can be calculated. The parameter C in equation (4) is the discharge coefficient for the orifice. For high Reynolds number the discharge coefficient is some constant value, but for low Reynolds number, where viscous forces play an important role, the discharge coefficient is a weak function of Reynolds number and hence of the fluid flowing through it. The empirical correlation for discharge coefficient in terms of ratio of diameters of orifice to pipe and Reynolds number is described below.

The above pressure drop equation is employed to calculate viscosity and density using the measured pressure drop values. This involves solving a non linear equation in density and viscosity. Two independent equations for two different choke sizes are used in this embodiment to calculate density and viscosity.

The correlation for discharge coefficient is given as:

$$C = \left(0.5991 + \frac{0.0044}{D} + \left(0.3155 + \frac{0.0175}{D}\right)(\beta^4 + 2\beta^{16})\right)\sqrt{1-\beta^4} + \quad (5)$$

$$\left(\frac{0.52}{D} - 0.192 + \left(16.48 - \frac{1.16}{D}\right)(\beta^4 + 4\beta^4)\right)\sqrt{\frac{1-\beta^4}{Re_D}}$$

where

C: Discharge Coefficient; D: Pipe Diameter (inches); $\beta$: Ratio of Orifice to Pipe Diameters; $Re_D$: Pipe Reynolds Number; A: Area of Choke; V: Velocity; Q: Flow Rate.

In the case considered, the flow is turbulent with a high Reynolds number. In such a case, the coefficient of discharge becomes independent of the Reynolds number and thus becomes a constant value. The sample calculations below show differential pressure between two points A and B in the flow line. This is not the pressure drop because of the pump that supplies a differential pressure inside the flow line. The differential pressure is calculated for varying viscosities and densities and for different choke combinations as well as for different flow rates. The following parameters can be varied to investigate the behavior of pressure difference between $P_A$ and $P_B$.

1. Flow rates which cause differing pump pressures.
2. Choke openings: Pressure loss will depend on which choke is constricted and which is kept open to flow.
3. Relative placement of chokes: This factor is relatively insignificant, as the spacing between the chokes is not very large.

Figure 6A:
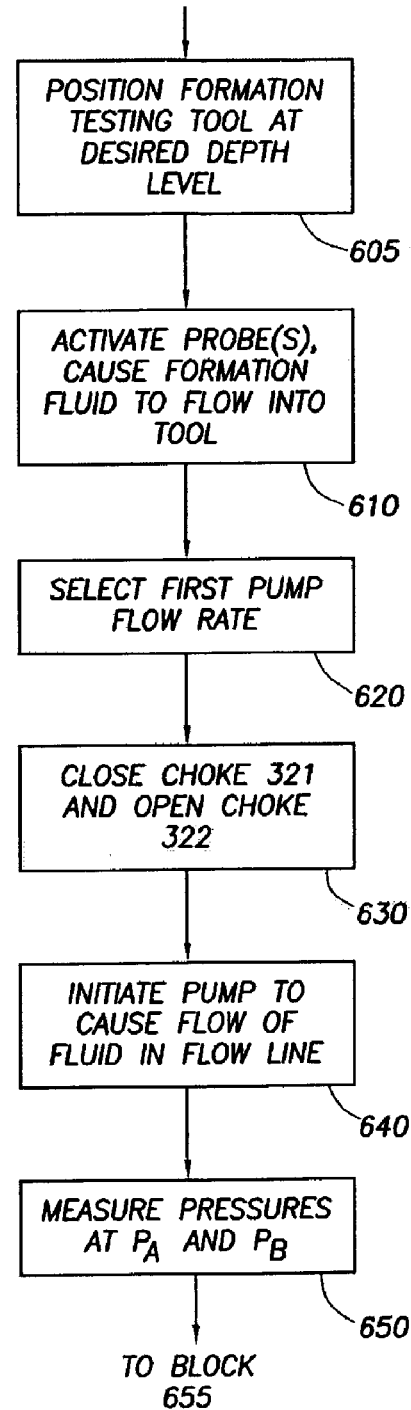
FIG. 6 is a diagram setting forth a sequence of steps in accordance with an embodiment of the invention.
Figure 7:
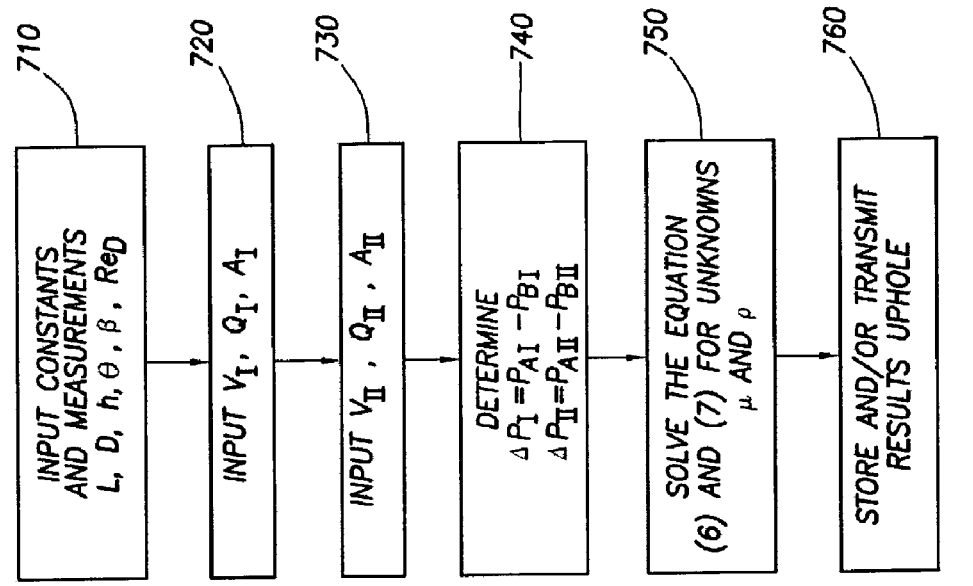
FIG. 7 is a flow diagram setting forth a sequence of steps in accordance with a portion of an embodiment of the invention.
Figure 6B:
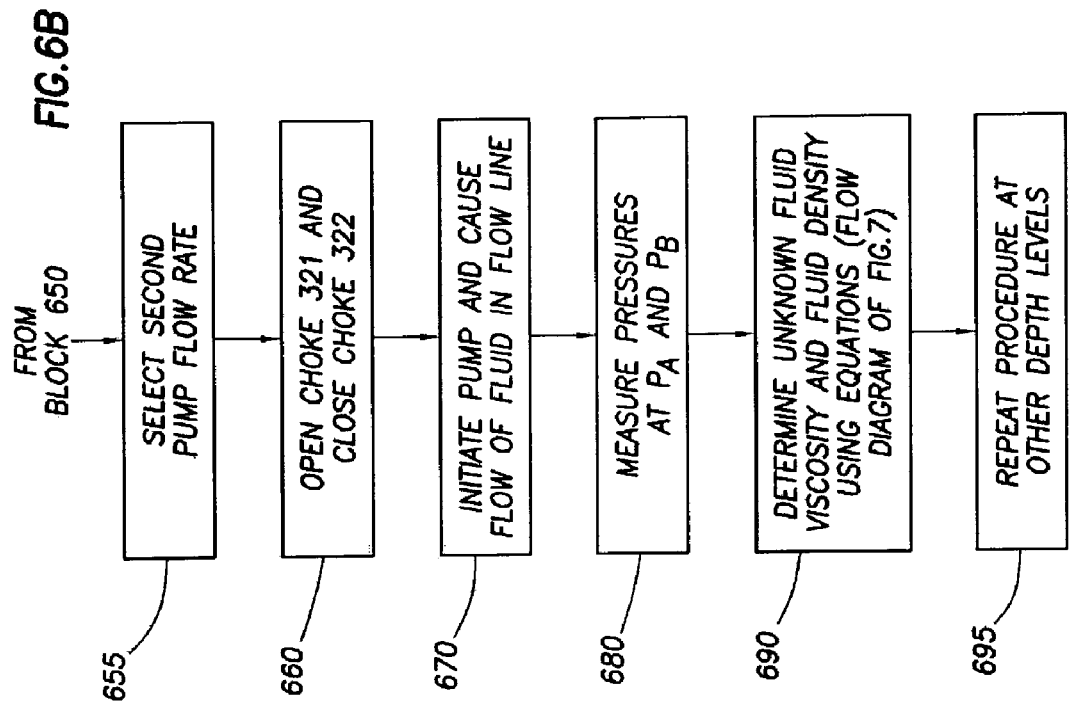

FIG. 6 is a flow diagram of steps of a method in accordance with an embodiment of the invention. The processor controlled steps can be under control of the uphole and/or downhole processors. The block 605 represents positioning of a formation testing tool, having features in accordance with the invention, at a desired depth level in the borehole. The block 610 represents activation of probe(s), in the tool, and the causing of formation fluid to flow in the tool and be collected in the tool. The block 620 represents setting of a first pump flow rate. Then, as represented by the block 630, the choke 321 is put in closed position and the choke 322 is put in an open position. The pump 310 is then initiated (block 640) causing flow of fluid in the line, and the pressures at gauges $P_A$ and $P_B$ are measured (block 650). Then, as represented by block 655, the second pump flow rate is set. The choke 322 is put in the closed position and the choke 321 is put in the open position (block 660). The pump is then initiated (block 670) to cause flow of fluid in the line. The pressures at gauges $P_A$ and $P_B$ are again measured (block 680). Then, as represented by the block 690, the routine described in conjunction with the flow diagram of FIG. 7 is performed to determine the fluid viscosity and fluid density. The block 695 represents repeating the procedure at other depth levels in the borehole.

As seen from equations (1) through (5), $\Delta P$ is a function of certain constants, known parameters, and unknown parameters, as follows: $\Delta P = f(\mu, \rho, V, L, D, h, \Theta, Q, \beta, A, Re_D)$.

The following are known or measured: L,D,h, $\theta$, $\beta$, $Re_D$. In the present embodiment, the following are set differently for the first operational condition (designated I) and the second operational condition (designated II): V,Q,A. The fluid viscosity ($\mu$) and density ($\rho$) are unknown. Thus, for operational condition I: $\Delta P_I = f(\mu, \rho, V_I, Q_I, A_I)$ (6) and for operational condition II: $\Delta P_{II} = f(\mu, \rho, V_{II}, Q_{II}, A_{II})$.

Figure 8:
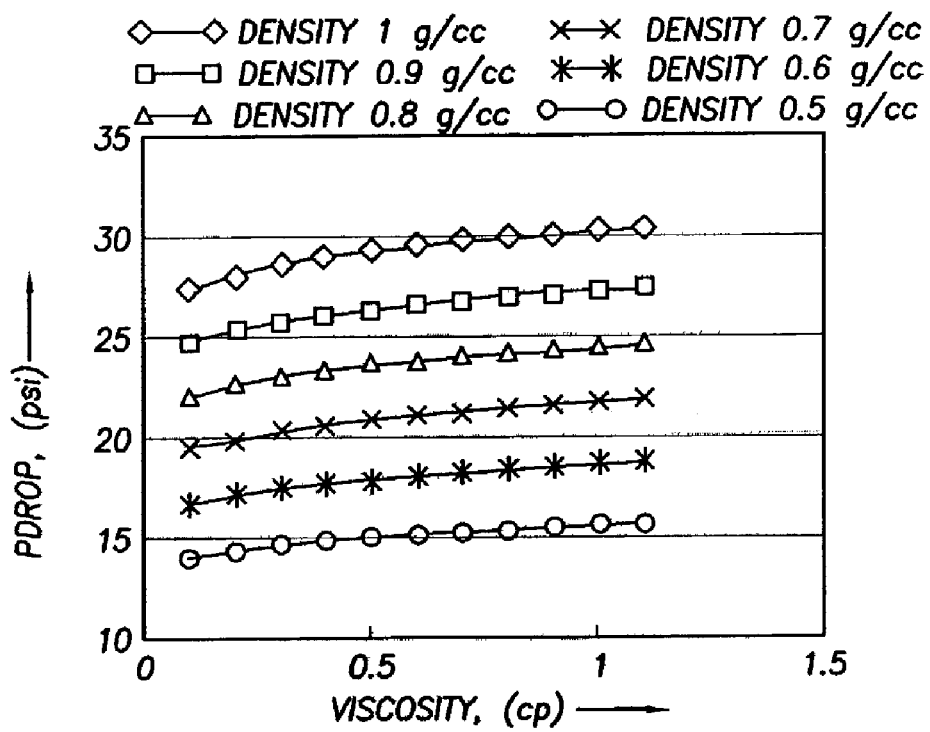
FIGS. 8–11 each sow graphs of viscosity versus pressure drop for different values of density, for particular choke sizes and flow rates.
Figure 9:
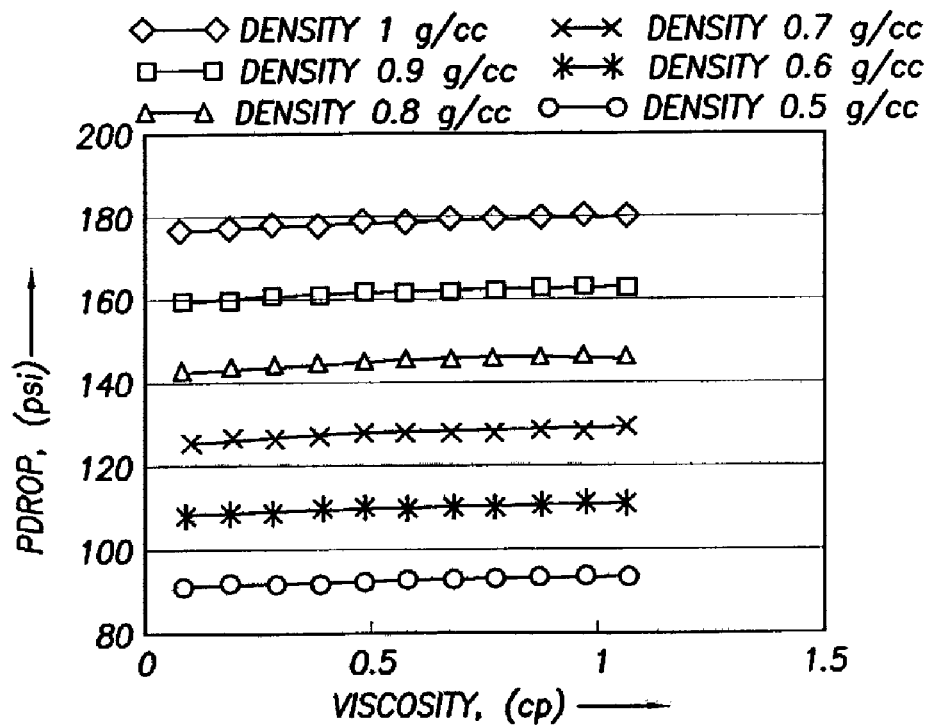
Figure 10:
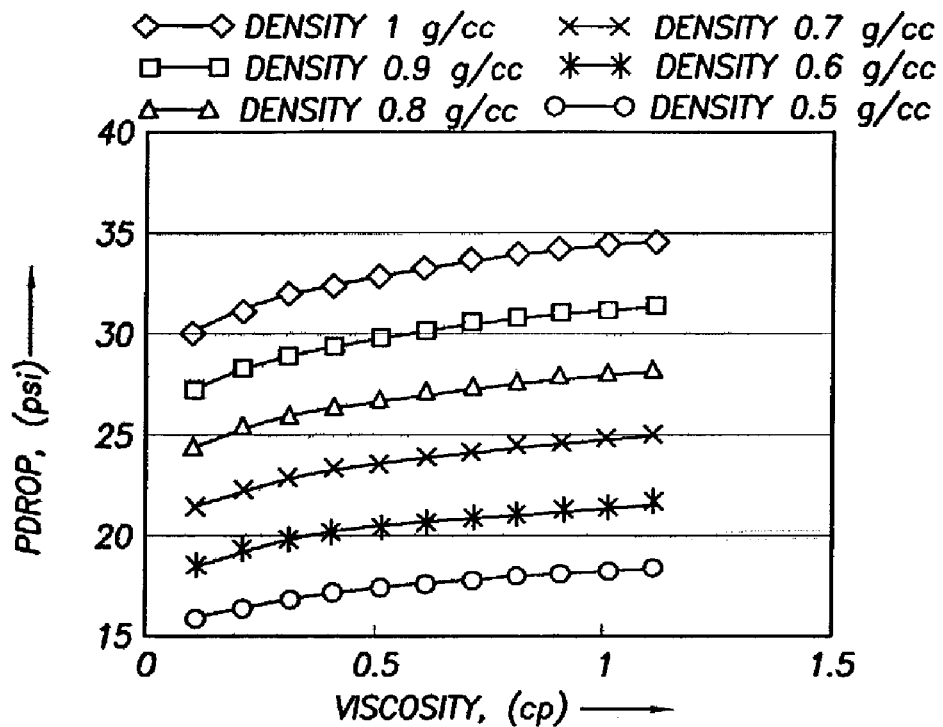
Figure 11:
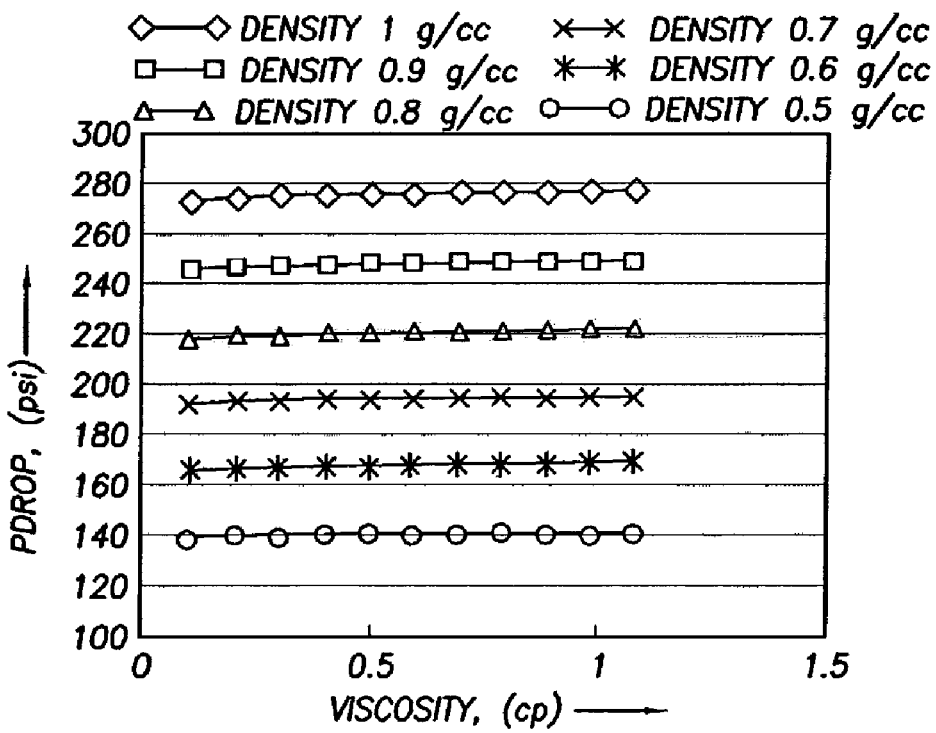

Accordingly, in the flow diagram of FIG. 7, the block 710 represents inputting, as constants or other selected values and/or measurements, L,D,h, $\theta$, $\beta$, $Re_D$. Then, known or set parameters for the first condition, $V_I, Q_I$, and $A_I$, are input (block 720), and the known (or set) parameters for the second condition, $V_{II}, Q_{II}$ and $A_{II}$, are input (block 730). Then, as represented by the block 740, the differential pressure for the first set of conditions is computed as the difference between the measured pressure $P_{AI}$ and the measured pressure $P_{BI}$, and the differential pressure for the second set of conditions is computed as the difference between the measured pressure $P_{AII}$ and the measured pressure $P_{BII}$. The two equations (6) and (7) can then readily be solved for the two unknowns, $\rho$ and $\mu$, using well known techniques, for example substitution or an iterative technique that converges toward a solution. These computations can be made downhole, uphole, or at a remote location. FIGS. 8, 9, 10 and 11 illustrate cases where two flow rates (0.45 and 0.35 gpm) are considered, and pump differential pressures are 1000 and 500 psi. The two chokes have diameters of 1 mm and 3 mm, respectively. For this example, the diameter of the flow line is 0.219 inches (0.0056 m) and is constant everywhere. FIG. 8 shows differential pressure between the points $P_A$ and $P_B$ for flow rate 0.35 gpm and pump pressure of 500 psi with smaller choke open and larger choke constricted. FIG. 9 shows the same case, but with the smaller choke constricted and the larger choke opened. FIGS. 10 and 11 show the cases where the flow rate is 0.45 gpm, and the pump pressure is 1000 psi. FIG. 10 shows the pressure profile for the case with the smaller choke opened and the larger choke constricted, and FIG. 11 shows the pressure profile for the case with the larger choke opened and the smaller choke constricted. From the foregoing plots it can be seen that, for the same flow rates the pressure loss is higher when the smaller choke is constricted. Also pressure drop increases with density (gravitational loss) and also increases with viscosity.

Figure 12:
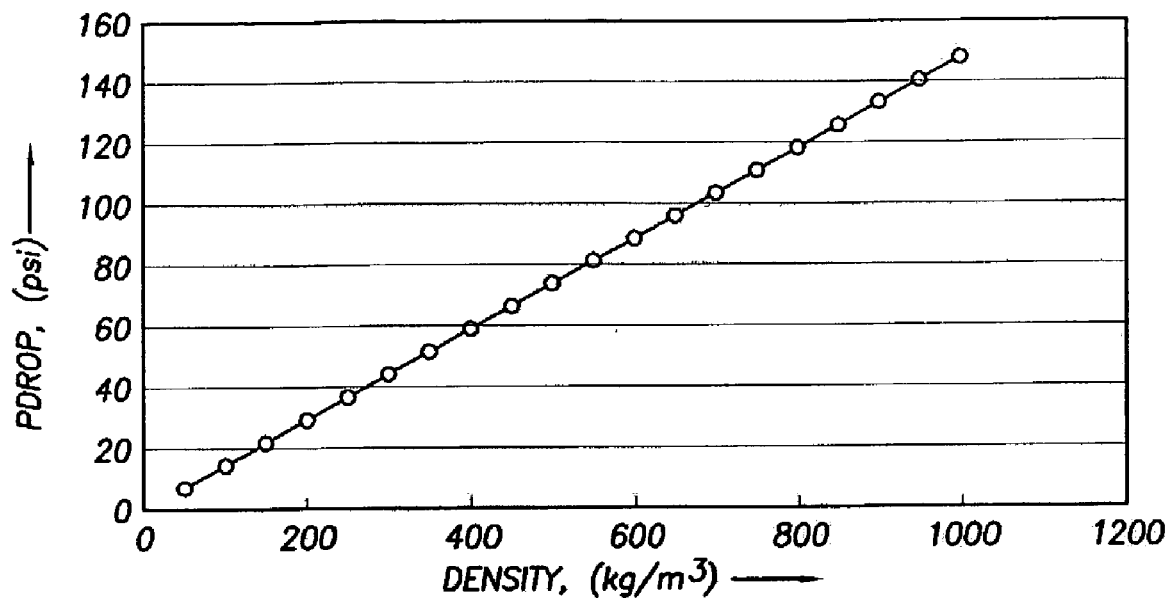
FIG. 12 is a graph of density versus pressure drop.
Figure 13:
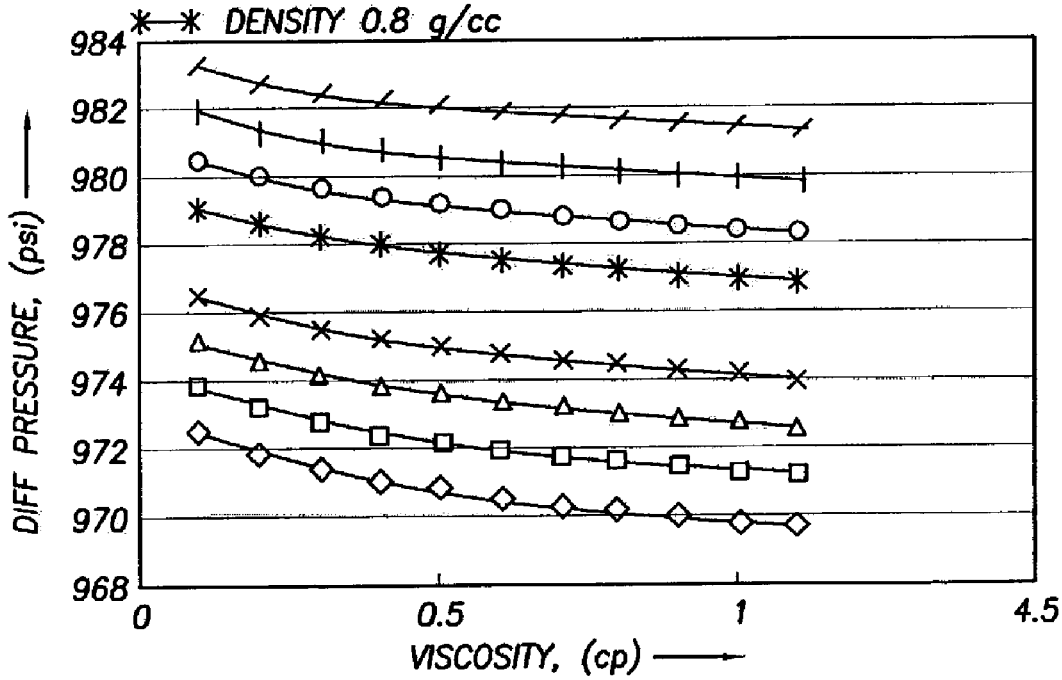
FIG. 13 is another graph of viscosity versus pressure drop for different values of density.

A further technique that can be used to determine viscosity and density, in accordance with a form hereof, is to use type curves. For calculating density, the differential pressure ($P_A$–$P_B$ as measured by the pressure gauges) is measured across the two points in a flow line. Two such readings are recorded, each with one choke open and the other constricted. It can be noted that the flow rate is not changed for this embodiment. The difference between these two readings will be proportional to the density of the fluid. This is because the flow is turbulent and hence the discharge coefficient of the choke is independent of viscosity of the fluid. Type curves for these readings for different densities are generated as shown in FIG. 12. When running the test in practice, two differential pressure readings with each choke constricted can be obtained. The difference between the two values of differential pressure can be plotted on to the illustrated graph to determine density. Once density is obtained the following type curves are used to calculate viscosity. The plot of FIG. 13 shows actual differential pressure plotted against viscosity. The plot corresponds to a fixed flow rate and choke size. Once density of the fluid is known, the viscosity is determined by using the measured differential pressure and the calculated density. FIG. 13 shows the variation of differential pressure with viscosity for a fixed flow rate and choke size and different densities.

The invention claimed is:

1. A method for determining viscosity and density of fluid from formations surrounding an earth borehole, comprising the steps of:
   (a) suspending a formation testing device in the borehole;
   (b) drawing formation fluid into the device;
   (c) causing said fluid to flow in a flow line under a first set of conditions and causing said fluid to flow in said flow line under a second set of conditions;
   (d) measuring a first fluid pressure differential across a portion of said flow line during fluid flow under said first set of conditions, and measuring a second pressure differential across said portion of said flow line during fluid flow under said second set of conditions; and
   (e) determining density and viscosity of said fluid as a function of said first and second measured pressure differentials.

2. The method as defined by claim 1, wherein said step of determining density and viscosity of said fluid includes deriving a first expression for the first measured pressure differential as a function of unknown fluid viscosity and fluid density at said first flow rate and deriving a second expression for the second measured pressure differential as a function of unknown fluid viscosity and fluid density at said second flow rate, and solving said first and second expressions to determine fluid viscosity and fluid density.

3. The method as defined by claim 1, further comprising repeating steps (b) through (e) at different depth levels in the borehole to determine the density and viscosity of fluid at said different depth levels in the formations.

4. The method as defined by claim 1, wherein said step of causing fluid to flow in said flow line under a first set of conditions includes providing a constriction in said flow line of different size than said first mentioned constriction.

5. The method as defined by claim 1, wherein said step of causing said fluid to flow in said flow line under a first set of conditions and under a second set of conditions includes providing a pump and a constriction in said flow line.

6. The method as defined by claim 5, wherein said pump is operated at a first flow rate during said first set of conditions and is operated at a second flow rate during said second set of conditions.

7. The method as defined by claim 5, wherein said step of measuring said first fluid pressure differential comprises providing pressure gauges on opposing sides of said constriction.

8. The method as defined by claim 7, wherein said step of causing fluid to flow in said flow line under a second set of conditions includes providing a constriction of different size than said first mentioned constriction in said flow line between said pressure gauges.

9. A method for determining viscosity and density of fluid from formations surrounding an earth borehole, comprising the steps of:
   (a) suspending a formation testing device in the borehole;
   (b) drawing formation fluid into the device;
   (c) causing said fluid to flow in a flow line in said device at a first flow rate and through a first constriction, and measuring a first pressure differential on opposing sides of the constriction;
   (d) causing said fluid to flow in a flow line of device at a second flow rate and through a second constriction, and measuring a second pressure differential on opposing sides of the second constriction; and
   (e) determining the density and viscosity of said fluid as a function of said first and second measured pressure differentials.

10. The method as defined by claim 9, wherein said providing of said first and second constrictions comprises providing first and second chokes having different opening areas.

11. The method as defined by claim 9, further comprising repeating steps (b) through (e) at different depth levels in the borehole to determine the density and viscosity of fluid at said different depth levels in the formations.

12. The method as defined by claim 9, wherein both of said causing steps utilize the same flow line.

13. The method as defined by claim 12, wherein said first and second constrictions are provided in said flow line.

14. The method as defined by claim 13, wherein said providing of said first and second constrictions comprises providing first and second chokes having different opening areas.

15. The method as defined by claim 14, further comprising controlling said first choke to be closed during said fluid flow at said first flow rate, and controlling said second choke to be closed during said fluid flow at said second flow rate.

16. The method as defined by claim 9, wherein said step of determining density and viscosity includes deriving a first expression for the first measured pressure differential as a function of unknown fluid viscosity and fluid density at said first flow rate and deriving a second expression for the second measured pressure differential as a function of unknown fluid viscosity and fluid density at said second flow rate, and solving said first and second expressions to determine fluid viscosity and fluid density.

17. The method as defined by claim 15, wherein said step of determining density and viscosity includes deriving a first expression for the first measured pressure differential as a function of unknown fluid viscosity and fluid density at said first flow rate and deriving a second expression for the second measured pressure differential as a function of unknown fluid viscosity and fluid density at said second flow rate, and solving said first and second expressions to determine fluid viscosity and fluid density.

18. Apparatus for determining viscosity and density of fluid from formations surrounding a borehole, comprising:
a formation testing device suspendible in the borehole, said device operating to draw fluid from surrounding formations and having a flow line in which said fluid can be caused to flow;
a first means for causing said fluid to flow in said flow line under a first set of conditions;
a second means for causing said fluid to flow in said flow line under a second set of conditions;
means for measuring a first fluid pressure differential in said portion of flow line during fluid flow under said first set of conditions, and for measuring a second pressure differential in said flow line during fluid flow under said second set of conditions; and
means for determining density and viscosity of said fluid as a function of said first and second measured pressure differentials.

19. Apparatus as defined by claim 18, wherein said means for determining density and viscosity of said fluid includes means for deriving a first expression for the first measured pressure differential as a function of unknown fluid viscosity and fluid density at said first flow rate and for deriving a second expression for the second measured pressure differential as a function of unknown fluid viscosity and fluid density at said second flow rate, and for solving said first and second expressions to determine fluid viscosity and fluid density.

20. Apparatus as defined by claim 18, wherein said first means for causing said fluid to flow in said flow line under a first set of conditions includes a pump and a constriction in said flow line.

21. Apparatus ad defined by claim 20, wherein said pump is operated at a first flow rate during said first set of conditions and is operated at a second flow rate during said second set of conditions.

22. Apparatus as defined by claim 20, wherein said constriction in said flow line comprises a choke.

23. Apparatus as defined by claim 20, wherein said constriction in said flow line comprises a remotely controllable choke.

24. Apparatus as defined by claim 20, wherein said first means for measuring said first fluid pressure differential comprises pressure gauges on opposing sides of said constriction.

25. Apparatus as defined by claim 24, wherein said second means for causing fluid to flow in said flow line under a second set of conditions includes said pump and a constriction of different size than said first mentioned constriction in said flow line between said pressure gauges.

26. Apparatus as defined by claim 20, wherein said second means for causing fluid to flow in said flow line under a second set of conditions includes said pump and a constriction in said flow line of different size than said first mentioned constriction.

27. Apparatus as defined by claim 26, wherein said constriction in said flow line comprises one position of a choke, and said different size constriction in said flow line comprises another position of said choke of different size opening.

28. Apparatus as defined by claim 26, wherein said constriction in said flow line comprises a choke, and said different size construction in said flow line comprises a different size choke.

29. Apparatus as defined by claim 26, wherein said pump is operated at a first flow rate during said first set of conditions and is operated at a second flow rate during said second set of conditions.

* * * * *